(12) United States Patent
DeAngelis

(10) Patent No.: US 10,028,856 B1
(45) Date of Patent: Jul. 24, 2018

(54) PROTECTIVE SHIELDS FOR PROTECTING THE LIMBS OF INJURED ANIMALS

(71) Applicant: Barbara DeAngelis, Staten Island, NY (US)

(72) Inventor: Barbara DeAngelis, Staten Island, NY (US)

( * ) Notice: Subject to any disclaimer, the term of this patent is extended or adjusted under 35 U.S.C. 154(b) by 0 days.

(21) Appl. No.: 15/412,140

(22) Filed: Jan. 23, 2017

(51) Int. Cl.
*A61F 5/00* (2006.01)
*A61F 5/058* (2006.01)
*A61F 13/00* (2006.01)
*A01K 13/00* (2006.01)

(52) U.S. Cl.
CPC ........ *A61F 5/05841* (2013.01); *A01K 13/007* (2013.01); *A61F 13/00004* (2013.01)

(58) Field of Classification Search
CPC .............. A61F 5/05858; A61F 5/05866; A61F 5/05841; A61F 5/0585; A61F 13/00004; A61F 2013/00093; A01K 13/007
USPC .......... 602/12, 5, 19, 20; 119/850; D24/190, D24/191
See application file for complete search history.

(56) References Cited

U.S. PATENT DOCUMENTS

| | | | | |
|---|---|---|---|---|
| 101,743 A * | 4/1870 | King | ........................ | A61F 13/04 24/484 |
| 323,775 A * | 8/1885 | Bender et al. | .......... | A61F 13/04 602/12 |
| 3,791,383 A | 2/1974 | Friedman | | |
| 4,465,064 A * | 8/1984 | Boone | ...................... | A61F 13/04 602/12 |
| 4,510,888 A * | 4/1985 | DeAngelis | ................ | A61D 9/00 119/850 |
| 4,727,865 A * | 3/1988 | Hill-Byrne | ............. | A61F 5/0111 24/68 SK |
| 7,753,864 B2 * | 7/2010 | Beckwith | ............... | A61F 5/0113 128/882 |
| 2016/0296357 A1 * | 10/2016 | Westover | ................. | A61F 5/012 |

* cited by examiner

*Primary Examiner* — Kim M Lewis
(74) *Attorney, Agent, or Firm* — Doherty IP Law Group LLC

(57) ABSTRACT

A protective shield having a tubular shape is used for protecting a wound on a limb of an animal. The protective shield includes a first sleeve half, a second sleeve half, and a hinge connecting the first and second sleeve halves for enabling the protective shield to move between open and closed positions. A first splint overlies the inner surface of said first sleeve half, and a first splint attachment strip is secured to the inner surface of the first sleeve half and extends between upper and lower ends of the first sleeve half. The first splint attachment strip has a plurality of splint mounting positions provided thereon for enabling the first splint to be secured to the first sleeve half at different locations between the upper and lower ends of the first sleeve half. A second splint overlies the inner surface of the second sleeve half, and a second splint attachment strip is secured to the inner surface of the second sleeve half and extends between upper and lower ends of the second sleeve half. The second splint attachment strip has a plurality of splint mounting positions provided thereon for enabling the second splint to be secured to the second sleeve half at different locations between the upper and lower ends of the second sleeve half.

20 Claims, 13 Drawing Sheets

US 10,028,856 B1

PROTECTIVE SHIELDS FOR PROTECTING THE LIMBS OF INJURED ANIMALS

BACKGROUND OF THE INVENTION

Field of the Invention

The present patent application is generally related to devices and tools for treating injured animals, such as dogs, and is more particularly related to protective shields that encircle and protect the limbs and/or legs of animals to permit healing of a wound, break, or injury, and to prevent the animal from accessing the injured site for facilitating the healing process.

Description of the Related Art

When treating humans after a disaster, accident, fire, or armed conflict, splints or stabilizing structures may be used while the patient is moved from a first location to a medical facility. Thus, a splint or stabilizing structure may be easily applied and ready for x-rays without removal upon arrival at the medical facility.

Animals may be injured due to vehicular accidents, or while running, jumping from heights, falling, slipping, or interacting with other animals. Animals may also suffer epidermal problems such as dry skin, rashes, burns and the like. Frequently, injured animals attempt to self-treat the injury by biting or licking the wound to alleviate the discomfort associated with the injury or skin condition. In some instances, animals may aggravate the injury to such an extent that a surgical procedure or destruction of the animal is required.

During post-treatment periods, animals often have a tendency to gnaw, chew or otherwise attempt to gain access to an injured location that may have stitches, topical dressings, splints or other medical treatments applied for healing purposes. These negative actions by animals tend to inhibit and prolong the recuperation period and may lead to secondary infections or injuries at the wound site.

There have been a number of attempts directed to providing a protective shield that prevents an animal from engaging in activities that prevent healing or exacerbate an injury. For example, U.S. Pat. No. 3,791,383 to Friedman discloses an injury protection device for four-legged animals including a tubular member having transversely opposed cut-out sections and harnessing means for securely attaching the device to the animal. The cut-out sections are adapted to enable the leg joints to have complete mobility, such that the movement of the animal is unimpaired. The device permits venting of the injury to the atmosphere to facilitate healing. The Freidman device tends to affect a rubbing of the skin about the support portion as well as portions about the leg over which the device is positioned, thereby aggravating the recuperative period.

Commonly owned U.S. Pat. No. 4,510,888 to DeAngelis et al., the disclosure of which is hereby incorporated by reference herein, teaches a protective shield assembly for an area of an animal to be protected. Referring to FIGS. 1-4, the protective assembly 10 is comprised of sleeve members 12, 14 having a semi-cylindrical shape that are mounted to one another by hinge members 16. The hinge members are comprised of half hinge elements 18 and 20 mounted, such as by welding, to the respective sleeve members 12, 14 and maintained in hinged relationship by a hinge pin 22.

The protective shield assembly 10 is formed with a securing assembly, generally indicated as 24, and comprised of a looped strap 26 including a buckle 28, mounted such as by rivets 30 to the member 12, and by a strap 32 mounted, such as by rivets 34 to the member 14.

Proximate the ends of the protective shield assembly 10 and mounted to inner surfaces of the members 12 and 14, such as by welding, there are provided inwardly-extending arm members 36. A semi-circular shaped support member 38 is mounted to paired arm members 36 in a manner to engage the leg of the animal, such as illustrated in FIG. 4. The semi-circular shaped support members 38 are formed of a metal or plastic and covered with a protective outer layer of a resilient material, such as rubber, foamed rubber, or the like.

The sleeve members 12, 14 may be formed of a metal, such as aluminum or stainless steel, or may be formed of a thermoplastic material, such as polycarbonate or like plastic material having physical properties to withstand the effects of gnawing or chewing by an animal. It will be understood by one skilled in the art that the hinge assemblies 16, buckle assembly 24, arm members 26, etc. are secured to the sleeve members 12, 14 by means compatible with the materials of construction of the sleeve members 12, 14. While a universal protective shield assembly would be desirable for any size animal, the protective shield assemblies are made in varying lengths and of varying spatial distances between the support member 38 and the sleeve members 12, 14.

DeAngelis teaches that during use, the injury to the animal is first cleaned and treated with an antiseptic material and a normal active treatment protocol performed whereupon the protective shield assembly 10 is caused to be encircled about the treated area of the leg of the animal in a manner such that the treated area is positioned between the semi-circular shaped support members 38, i.e. out of contact with the treated area to minimize aggravation to the injury wound. The strap 32 is positioned within the buckle 28 and drawn fast to a point whereby the force between the support members 38 and the leg of the animal is sufficient to maintain the protective shield assembly 10 at the desired position, but with a support force that is insufficient to cause discomfort to the animal or to aggravate the treatment protocol by reducing circulation to the injury or wound.

In spite of the above advances, there remains a need for improved protective shields for the limbs of animals that are transparent, light-weight, and adjustable. There also remains a need for a protective shield for an animal that has splints that are adjustable for accommodating different types of limbs, injuries and animals.

SUMMARY OF THE INVENTION

In one embodiment, a protective shield having a tubular shape for protecting a wound on a limb of an animal includes a first sleeve half having a semi-cylindrical shape and a second sleeve half having a semi-cylindrical shape. In one embodiment, the first and second sleeve halves are adapted to be joined together for forming a tubular shaped protective shield. In one embodiment, the inner surfaces of the first and second sleeve halves define a central opening adapted to receive a limb of an animal.

In one embodiment, the protective shield desirably includes a first splint configured to be secured to the first sleeve half, the first splint having an arc-shaped body with a top surface having a concave shape that is adapted to contact the limb of the animal.

In one embodiment, the protective shield includes a first splint attachment strip secured to the inner surface of the first sleeve half and extending between upper and lower ends of the first sleeve half. The first splint attachment strip preferably has a plurality of splint mounting positions provided thereon for securing the first splint to the first sleeve half at different locations between the upper and lower ends of the first sleeve half.

In one embodiment, the plurality of splint mounting positions on the first splint attachment strip may include a first mounting position for securing the first splint to the first sleeve half at a first location that is closer to the upper end of the first sleeve half, a second mounting position for securing the first splint to the first sleeve half at a second location that is equidistant from the upper and lower ends of the first sleeve half, and a third mounting position for securing the first splint to the first sleeve half at a third location that is closer to the lower end of the first sleeve half. Other first splint attachment strips may have fewer or more mounting positions for adjusting the position of the first splint and still fall within the scope of the present invention.

In one embodiment, the first splint desirably has a bottom surface that faces away from the top surface of the first splint, the bottom surface being spaced from and opposing the inner surface of the first sleeve half. In one embodiment, the bottom surface of the first splint has a convex curved surface. In one embodiment, the first splint desirably includes first splint support legs projecting from the bottom surface of the first splint, the first splint support legs having lower ends that slope for conforming to the shape of the inner surface of the first sleeve half. In one embodiment, the first splint has four support legs that are positioned in four corners of the body of the first splint.

In one embodiment, the first splint may have first splint locking projections that extend from the bottom surface of the first splint. In one embodiment, the first splint locking projections are configured for forming a snap-fit connection with the splint mounting positions provided on the first splint attachment strip. In one embodiment, the first splint has two first splint locking projections that extend from the bottom surface of the body of the first splint.

In one embodiment, the protective shield desirably includes a second splint configured to be secured to the second sleeve half for opposing the first splint, the second splint having an arc-shaped body with a top surface having a concave shape that is adapted to contact the limb of the animal.

In one embodiment, the protective shield preferably has a second splint attachment strip secured to the inner surface of the second sleeve half and extending between upper and lower ends of the second sleeve half, whereby the second splint attachment strip has a plurality of splint mounting positions provided thereon for securing the second splint to the second sleeve half at different locations between the upper and lower ends of the second sleeve half.

In one embodiment, the splint mounting positions on the second splint attachment strip preferably include a first mounting position for securing the second splint to the second sleeve half at a first location that is closer to the upper end of the second sleeve half, a second mounting position for securing the second splint to the second sleeve half at a second location that is equidistant from the upper and lower ends of the second sleeve half, and a third mounting position for securing the second splint to the second sleeve half at a third location that is closer to the lower end of the second sleeve half. Other second splint attachment strips may have fewer or more mounting positions for adjusting the position of the second splint and still fall within the scope of the present invention.

In one embodiment, the second splint may have a bottom surface that faces away from the top surface of the second splint, the bottom surface being spaced from and opposing the inner surface of the second sleeve half. In one embodiment, the second splint has second splint support legs that project from the bottom surface of the second splint. In one embodiment, the second splint support legs having lower ends that slope for conforming to the shape of the inner surface of the second sleeve half. In one embodiment, the second splint has four support legs that are positioned in four corners of the body of the second splint.

In one embodiment, the second splint has second splint locking projections that extend from the bottom surface of the second splint. In one embodiment, the second splint locking projections are configured for forming a snap-fit connection with the splint mounting positions provided on the second splint attachment strip.

In one embodiment, the protective shield preferably has a hinge connecting the first and second sleeve halves together for enabling the protective shield to move between open and closed positions. In one embodiment, the first and second sleeve halves have opposing free edges that are spaced from one another when the protective shield is in the open position and abut one another when the protective shield is in the closed position.

In one embodiment, the protective shield desirably has a first securing band provided on the second sleeve half, the first securing band having a free end that extends beyond the free edge of the second sleeve half, and a first recess formed in an outer surface of the first sleeve half that extends to the free edge of the first sleeve half. In one embodiment, when the protective shield is in the closed position, the free end of the first securing band is seated in the first recess formed in the outer surface of the first sleeve.

In one embodiment, a first locking projection extends from the free end of the first securing band, and a first locking hole is formed in the first recess. In one embodiment, the first locking projection on the first securing band is adapted to be inserted into the first locking hole formed in the first recess for holding the protective shield in the closed position.

In one embodiment, the protective shield desirably includes a second securing band provided on the second sleeve half, the second securing band having a free end that extends beyond the free edge of the second sleeve half, and a second recess formed in the outer surface of the first sleeve half that extends to the free edge of the first sleeve half. In one embodiment, when the protective shield is in the closed position, the free end of the second securing band is seated in the second recess formed in the outer surface of the first sleeve.

In one embodiment, a second locking projection extends from the free end of the second securing band, and a second locking hole is formed in the second recess. In one embodiment, the second locking projection on the second securing band is inserted into the second locking hole formed in the second recess for holding the protective shield in the closed position.

In one embodiment, the protective shield is transparent and may be made of polymer materials such as polypropylene.

In one embodiment, a pad may be secured over the top surface of the first splint and/or the second splint. In one embodiment, the pad is selected from the group consisting of gauze, cushioning, surgical mesh, and sanitary dressings.

In one embodiment, the pad is a disposable, peel and stick pad that may be secured to the top surfaces of the first and second splints.

In one embodiment, a protective shield for protecting a wound on a limb of an animal has a tubular shape and is made of a transparent, polymer material. In one embodiment, the protective shield desirably includes a first sleeve half having a semi-cylindrical shape, a second sleeve half having a semi-cylindrical shape, and a hinge connecting the first and second sleeve halves together for enabling the protective shield to move between open and closed positions. In one embodiment, the inner surfaces of the first and second sleeve halves define concave curved surfaces. In one embodiment, the inner surfaces of the first and second sleeve halves define a central opening adapted to receive a limb of an animal;

In one embodiment, the protective shield desirably has a first splint overlying the inner surface of the first sleeve half, the first splint having an arc-shaped body with a top surface having a concave shape that is configured to contact the limb of the animal, and a first splint attachment strip secured to the inner surface of the first sleeve half and extending between upper and lower ends of the first sleeve half. In one embodiment, the first splint attachment strip preferably has a plurality of splint mounting positions provided thereon for securing the first splint to the first sleeve half at different locations between the upper and lower ends of the first sleeve half.

In one embodiment, the protective shield desirably has a second splint overlying the inner surface of the second sleeve half, the second splint having an arc-shaped body with a top surface having a concave shape that is configured to contact the limb of the animal, and a second splint attachment strip secured to the inner surface of the second sleeve half and extending between upper and lower ends of the second sleeve half. In one embodiment, the second splint attachment strip preferably has a plurality of splint mounting positions provided thereon for securing the second splint to the second sleeve half at different locations between the upper and lower ends of the second sleeve half.

In one embodiment, the splint mounting positions on the first splint attachment strip include a first mounting position for securing the first splint to the first sleeve half at a first location that is closer to the upper end of the first sleeve half, a second mounting position for securing the first splint to the first sleeve half at a second location that is equidistant from the upper and lower ends of the first sleeve half, and a third mounting position for securing the first splint to the first sleeve half at a third location that is closer to the lower end of the first sleeve half.

In one embodiment, the splint mounting positions on the second splint attachment strip preferably include a first set of mounting holes for securing the second splint to the second sleeve half at a first location that is closer to the upper end of the second sleeve half, a second set of mounting holes for securing the second splint to the second sleeve half at a second location that is equidistant from the upper and lower ends of the second sleeve half, and a third set of mounting holes for securing the second splint to the second sleeve half at a third location that is closer to the lower end of the second sleeve half.

In one embodiment, the first splint preferably has a bottom surface that faces away from the top surface of the first splint, the bottom surface being spaced from and opposing the inner surface of the first sleeve half, first splint support legs projecting from the bottom surface of the first splint, the first splint support legs having lower ends that slope for conforming to the shape of the inner surface of the first sleeve half, and first splint locking projections extending from the bottom surface of the first splint. In one embodiment, the first splint locking projections are configured for forming a snap-fit connection with the splint mounting positions on the first splint attachment strip.

In one embodiment, the second splint preferably has a bottom surface that faces away from the top surface of the second splint, the bottom surface being spaced from and opposing the inner surface of the second sleeve half, second splint support legs projecting from the bottom surface of the second splint, the second splint support legs having lower ends that slope for conforming to the shape of the inner surface of the second sleeve half, and second splint locking projections extending from the bottom surface of the second splint. In one embodiment, the second splint locking projections are configured for forming a snap-fit connection with the mounting positions on the second splint attachment strip.

In one embodiment, the first and second sleeve halves preferably have opposing free edges that are spaced from one another when the protective shield is in the open position and abut one another when the protective shield is in the closed position.

In one embodiment, the protective shield includes a first securing band that is provided on the second sleeve half adjacent the upper end of the second sleeve half. The first securing band preferably has a free end that extends beyond the free edge of the second sleeve half.

In one embodiment, a first recess is formed in an outer surface of the first sleeve half that extends to the free edge of the first sleeve half. In one embodiment, when the protective shield is in the closed position, the free end of the first securing band is seated in the first recess formed in the outer surface of the first sleeve;

In one embodiment, the protective shield includes a second securing band provided on the second sleeve half adjacent the lower end of the second sleeve half, the second securing band having a free end that extends beyond the free edge of the second sleeve half.

In one embodiment, a second recess formed in the outer surface of the first sleeve half that extends to the free edge of the first sleeve half. In one embodiment, when the protective shield is in the closed position, the free end of the second securing band is seated in the second recess formed in the outer surface of the first sleeve.

In one embodiment, the protective shield preferably includes pads secured over the top surfaces of the respective first and second splints. In one embodiment, the pads may include gauze, cushioning material, surgical mesh, and/or and sanitary dressings.

In one embodiment, a protective shield provides a tubular, high-impact, light-weight, transparent protective unit that encircles and protects a limp to permit healing of a wound, break or burn, and to substantially prevent continued self-destruction of the healing process. A conventional cast must be removed to x-ray, re-medicate an injury, or monitor an injury. The protective shield disclosed herein may be easily applied to and removed from a limb. In one embodiment, it is made of high-impact, non-toxic transparent plastic hinge shield with two internal adjustable splints, and a disposable peel and stick sanitary pad that is positioned over the splints. In one embodiment, the disposable pads allow for a total sanitary condition which also allows the splint to be sanitized and reused with new sanitary pads.

In one embodiment, the transparent or see-through plastic allows for x-rays without removing the protective shield.

The transparent protective shield also allows for constant monitoring of the wound without removing the shield from a limb. In one embodiment, the protective shield may be easily opened for re-medicating the wound without completely removing the unit from the limb.

In one embodiment, the adjustability of the splints allows targeted use at the site of an injury, thus enabling an animal to bend and use its paws to walk or run, or a human to have full use of his or her hands or feet. The protective shield also enables air to flow there through to promote quicker healing, and the adjustable splints enable the protective shield to be adjustable for responding to swelling conditions. Because the protective shield is simple, portable, and light-weight, it is adapted for rapid application by medical personnel at accident and disaster sites. When used for animals, veterinarians may take it along with them to farms, zoos, and inaccessible sites so that animals do not have to be brought into the office for a visit.

In one embodiment, the protective shield is made of a transparent material, such as plastic, or polypropylene. In one embodiment, the protective shield includes first and second sleeve halves that are hingedly connected together so that the sleeve halves may be moved between an open configuration and a closed configuration.

In one embodiment, each of the two sleeve halves have splint adjustment strips that extend between the respective upper and lower ends of the sleeve halves. In one embodiment, the splint adjustment strips have openings or holes for snap-fitting splints to the strips for attaching them to the inner surfaces of the first and second sleeve halves. In one embodiment, each strip has a plurality of holes extending along the length thereof so that the position of the splint may be adjusted along the length of the strips. In one embodiment, one or both of the splints may be removed from their attachment to the strips. In one embodiment, only one splint is used and a splint is not attached to the opposing splint adjustment strip.

In one embodiment, a disposable peel and stick pad is attached to top surfaces of the splints. The peel and stick pads are disposable and may be replaced for sanitary purposes. The peel and stick and pads have padding to create a comfortable surface for the splint so that no secondary wound is rubbed and/or created.

In one embodiment, an outside flexible strap is not utilized for holding the first and second sleeve halves together. In the prior art, an outer strap was utilized, however, an animal such as a dog could chew on the strap, loosening it, and causing the protective shield to open. In order to overcome these deficiencies, in one embodiment, two securing bands extend from a free edge of a first sleeve half and the opposing sleeve half has recesses that receive the free ends of the securing bands. As a result, the securing bands are seated within the recesses so that an animal cannot access and/or chew on the bands. The free ends of the bands include snap-fit projections that are adapted to snap-fit into openings on the opposing sleeve half.

In one embodiment, the protective shield is made of heavy duty, transparent, polypropylene so that a limb may be x-rayed without removing the protective shield.

In one embodiment, a waterproof sleeve may be placed over the outer surface of the protective shield to protect the ends of the shield and a wound when an animal is working and walking as to keep out rain, mud, snow and harmful elements.

In one embodiment, the protective shield is made of clear, transparent, polypropylene which is non-toxic, and FDA approved for use with animals. Providing a transparent protective shield enables medical personnel and owners to monitor a wound at all times without removing the protective shield from a limb. In addition, a non-metal transparent polypropylene protective shield enables a limb to be x-rayed without removing the protective shield from the limb. The use of relatively light-weight polypropylene materials provides for a portable protective shield that may be worn by an animal when walking, running, and working. Thus, the protective shield may be worn during normal activities as a wound heals.

In one embodiment, the upper and lower ends of the first and second sleeve halves of the protective shield have rounded corners and no sharp edges that may create secondary wounds.

In one embodiment, the protective shield may be formed using injection molding techniques.

The protective shield disclosed herein may be utilized for all types of animals including dogs, cats, farm animals, wild animals, and humans.

These and other preferred embodiments of the present invention will be described in more detail below.

DETAILED DESCRIPTION OF PREFERRED EMBODIMENTS

Figure 1:
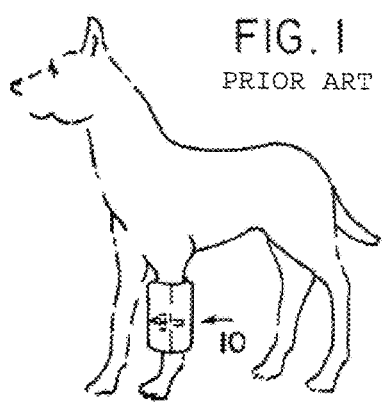
FIG. 1 shows a prior art protective shield assembly positioned on a leg of a canine.
Figure 4:
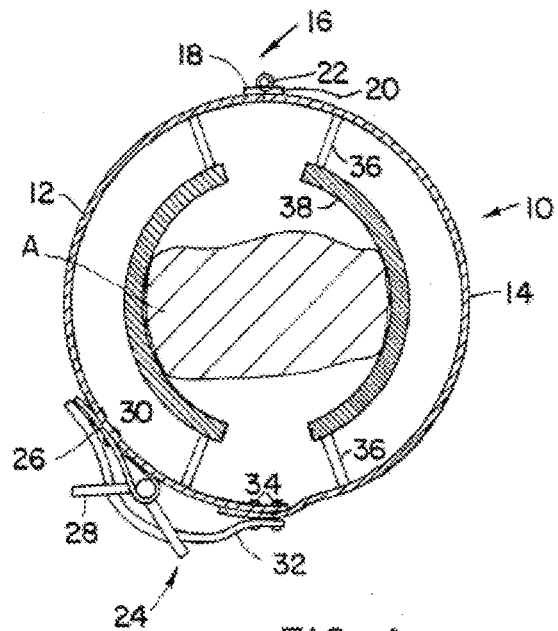
FIG. 4 is a side view of the prior art protective shield assembly shown in FIG. 2.
Figure 2:
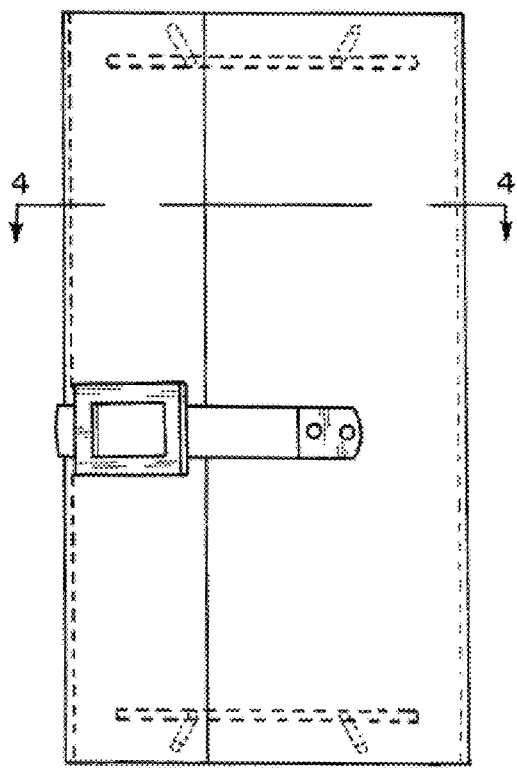
FIG. 2 is a plan view of the prior art protective shield assembly shown in FIG. 1.
Figure 3:
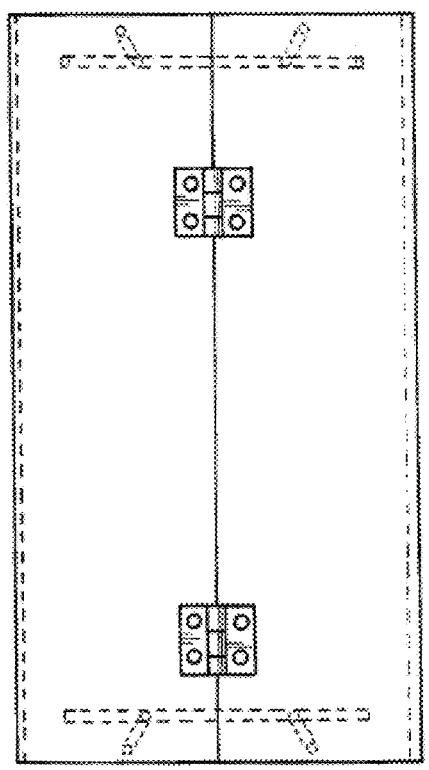
FIG. 3 is a back view of the prior art protective shield assembly shown in FIG. 2.
Figure 5:
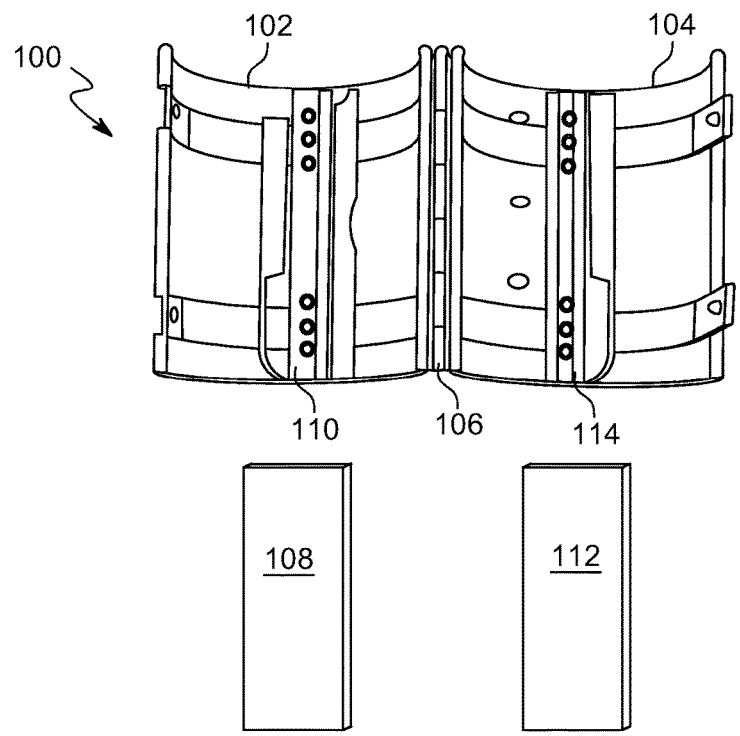
FIG. 5 shows a protective shield for an animal including first and second sleeve halves and first and second adjustable splints, in accordance with one embodiment of the present invention.

Referring to FIG. 5, in one embodiment, a protective shield 100 for an animal preferably includes a first sleeve half 102 and a second sleeve half 104 that are coupled to one another via a hinge 106 that enables the protective shield to move between open and closed positions. In one embodiment, the protective shield 100 desirably includes a first adjustable splint 108 adapted to be secured to a splint adjustment strip 110 on the first sleeve half 102 and a second adjustable splint 112 adapted to be secured to a second splint adjustment strip 114 on the second sleeve half 104. The positions of the splints on the adjustment strips are preferably adjustable for accommodating different types of medical situations, and different types of limbs, animals and injuries.

Figure 6:
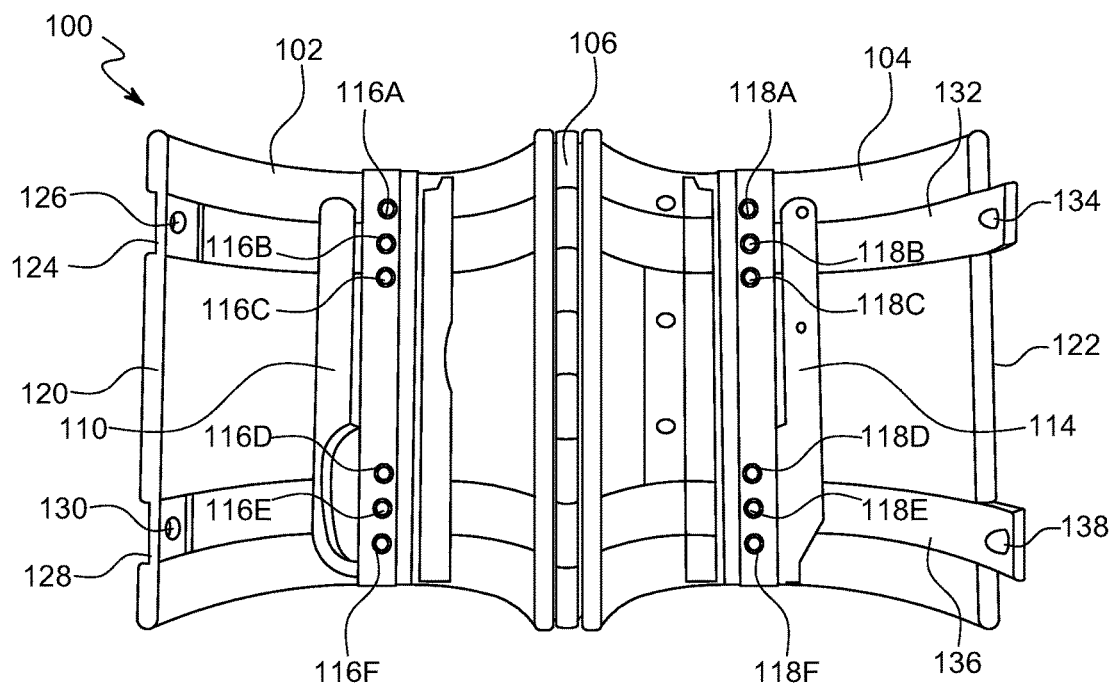
FIG. 6 shows the first and second sleeve halves of the protective shield shown in FIG. 5 including a first splint adjustment strip on the first sleeve half and a second splint adjustment strip on the second sleeve half.

Referring to FIG. 6, in one embodiment, the first splint adjustment strip 110 preferably includes a series of adjustment holes 116A-116F provided thereon. In one embodiment, the adjustment holes 116A-116F are vertically aligned with one another along the length of the first sleeve half 102. In one embodiment, the first splint adjustment strip 110 preferably extends between the upper and lower ends of the first sleeve half 102. In one embodiment, the adjustment holes 116A-116F are paired with one another to provide different adjustment heights on the first splint adjustment stip. In one embodiment, the adjustment holes 116A and 116D are used to connect the first splint to the first splint adjustment strip 110 at a first location that is closer to the upper end of the first sleeve half 102. In one embodiment, the adjustment holes 116B and 116E are used to connect the first splint to the first splint adjustment strip 110 at a second location that is equidistant between the upper and lower ends of the first sleeve half 102. In one embodiment, the adjustment holes 116C and 116F are used to connect the first splint to the first splint adjustment strip 110 at a third location that is closer to the lower end of the first sleeve half 102. In other embodiments, the first splint adjustment strip may have fewer or more mounting locations (e.g., five different mounting positions) and still fall within the scope of the claims.

In one embodiment, the second splint adjustment strip 114 on the second sleeve half 104 preferably includes a series of adjustment holes 118A-118F extending along the length of the second splint adjustment strip 114. In one embodiment, the adjustment holes 118A-118F are paired with one another to provide different adjustment heights on the second splint adjustment strip. In one embodiment, the adjustment holes 118A and 118D are used to connect the second splint 112 to the second splint adjustment strip 114 at a first location that is closer to the upper end of the second sleeve half 104. In one embodiment, the adjustment holes 118B and 118E are used to connect the second splint 112 to the second splint adjustment strip 114 at a second location that is equidistant between the upper and lower ends of the second sleeve half 104. In one embodiment, the adjustment holes 118C and 118F are used to connect the second splint 112 to the second splint adjustment strip 114 at a third location that is closer to the lower end of the second sleeve half 104.

In one embodiment, the hinge 106 enables the first sleeve half 102 and the second sleeve half 104 to be moved between the open position shown in FIG. 6 and a closed position (FIG. 12B) whereby the free edges 120, 122 of the respective first and second sleeve halves 102, 104 abut one another. In one embodiment, the first sleeve half 102 includes a first recess 124 having an opening 126 formed therein adjacent an upper end of the first sleeve half 102. The first sleeve half 102 also includes a second recess 128 having a second opening 130 adjacent a lower end of the first sleeve half 102.

In one embodiment, the second sleeve half 104 has a first securing band 132, adjacent the upper end of the second sleeve half 104, with a first projection 134 that is adapted to be seated within the first hole 126 within the first recess 124 of the first sleeve half 102. The second sleeve half 104 also includes a second securing band 136, adjacent the lower end of the second sleeve half 104, having a projection 138 adapted to be received within the second opening 130 of the second recess 128 at the lower end of the first sleeve half 102. In one embodiment, when the protective shield is closed, the free edges 120, 122 of the respective first and second sleeve halves 102, 104 abut one another with the first and second projections 134, 138 inserted into the respective openings 126, 130, and the portion of the bands 132, 136 extending beyond the free edge 122 being seated within the respective recesses 124, 128 of the first sleeve half 102. In one embodiment, the securing bands 132, 136 are made of polypropylene. Seating the bands within the recesses 124, 128 desirably prevents an animal from accessing the bands and chewing and/or destroying the bands. In one embodiment, the projections 134, 138 and the respective bands 132, 136 enable the first and second sleeve halves 102, 104 to be securely closed together for enhancing the strength of the protective shield 100 when in a closed configuration.

Figure 7A:
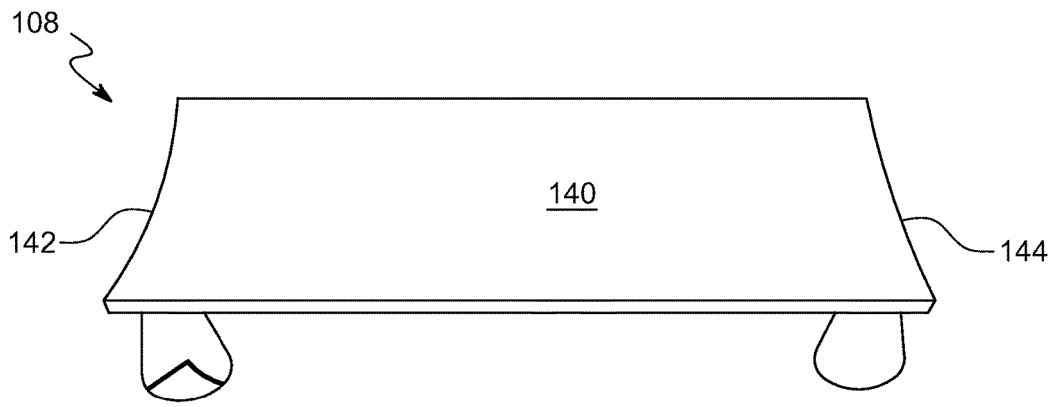
FIGS. 7A-7D show perspective, end view, bottom view, and top plan view of the first adjustable splint shown in FIG. 5.

Referring to FIG. 7A, in one embodiment, the first adjustable splint 108 has a body with a top surface 140 that is adapted to abut against an outer surface of an animal's appendage. In one embodiment, the top surface 140 is concave or arcuate and extends from a first end 142 to a second end 144 of the body of the first adjustable splint 108.

Figure 7B:
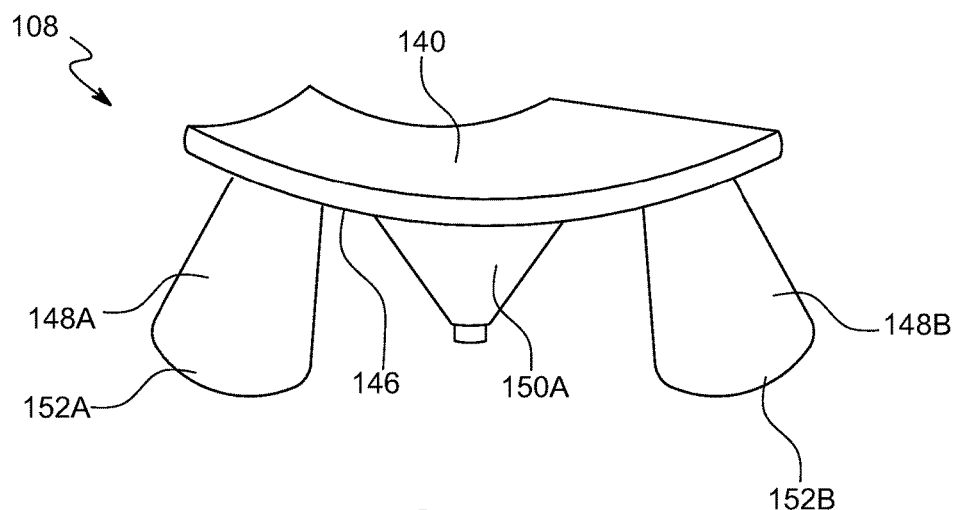

Referring to FIG. 7B, in one embodiment, the first adjustable splint 108 has a body with a top surface 140 that defines a concave shape and a bottom surface 146 that defines a convex shape. The first adjustable splint 108 includes support legs 148A, 148B that project from the bottom surface 146 and snap-fit projections 150A, 150B (FIG. 7C) that also project from the bottom surface 146. In one embodiment, the lower ends 152 of the support legs 148A, 148B have sloping surfaces that generally conform to and/or match the concave curved shape of the top surface 140 of the first adjustable splint 108. As shown in FIG. 7B, the slope at the lower end 152A of the first support leg 148A is different from the slope at the lower end 152B of the second support leg 148B, however, the respective sloping surfaces match the contour of the concave top surface 140 of the first adjustable splint 108. The sloping surfaces at the bottom ends of the support legs 148 also preferably conform to the concave, inner surfaces of the first and second sleeve halves 102, 104 (FIG. 6).

Figure 7C:
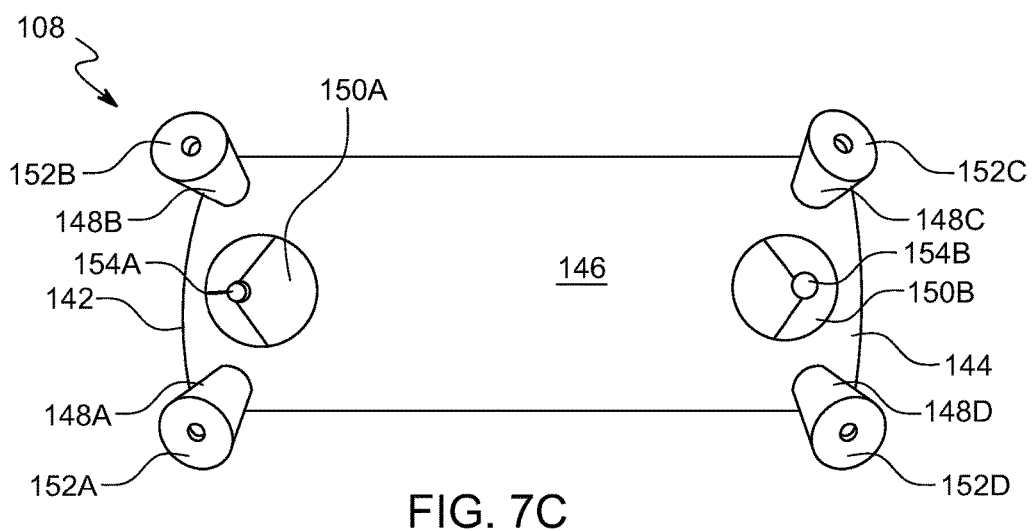

Referring to FIG. 7C, in one embodiment, the first adjustable splint 108 preferably includes first and second support legs 148A, 148B projecting from the bottom surface 146 adjacent the first end 142, and third and fourth support legs 148C, 148D projecting from the bottom surface adjacent the second end 144. The first adjustable splint 108 also desirably includes a first snap-fit projection 150A adjacent the first end 142 and a second snap-fit projection 150B adjacent the second end 144. The respective knobs 154A, 154B at the apexes of the snap-fit projections 150A, 150B are adapted to the snap-fit into the adjustment holes 116A-116F, 118A-18F provided on the respective first and second splint adjustment strips 110, 114 (FIG. 6). The respective bottom surfaces 152A-152D of the support legs 148A-148D preferably slope and conform to the concave curve of the top surface 140 (FIG. 7B) of the first adjustable splint 108 or the concave inner surfaces of the first and second sleeve halves.

In one embodiment, after the first adjustable splint 108 has been secured to one of the sleeve halves of the protective shield, the concave top surface 140 may be abutted against an outer surface of an animal's appendage. In one embodiment, the first and second splints contact locations on the limb that are not wounded, and the wound site on the limb is positions between the splints so the splints are not in contacts with the wound(s).

Figure 7D:
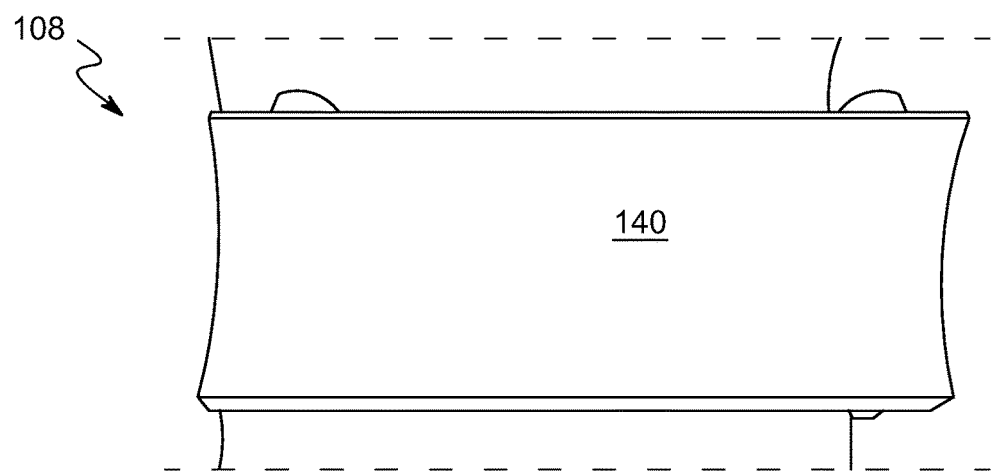
Figure 8:
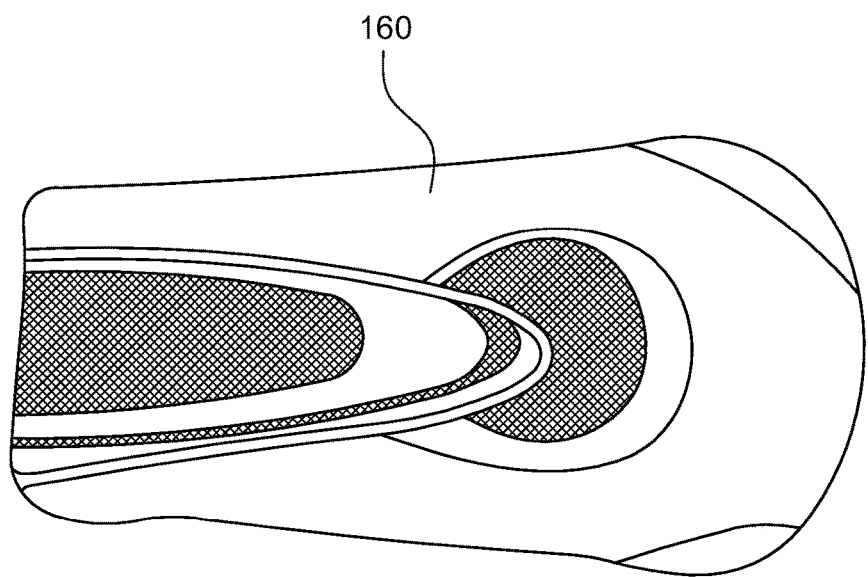
FIG. 8 shows a sanitary pad secured over the first adjustable splint shown in FIG. 7A-7D, in accordance with one embodiment of the present invention.

Referring to FIG. 8, in one embodiment, a sanitary pad or gauze 160 may be positioned over the top surface 140 of the first adjustable splint 108 (FIG. 7D). In one embodiment, the sanitary pad or gauze comprises a peel and stick pad for the splint, which is disposable and may be replaced for sanitary purposes. In one embodiment, the peel and stick pad and/or gauze creates a padded, comfortable surface for the splint so that no secondary wound is created by friction.

In one embodiment, the second splint 112 (FIGS. 5 and 6) has the same shape, structure and configuration as the first splint described above.

Figure 9A:
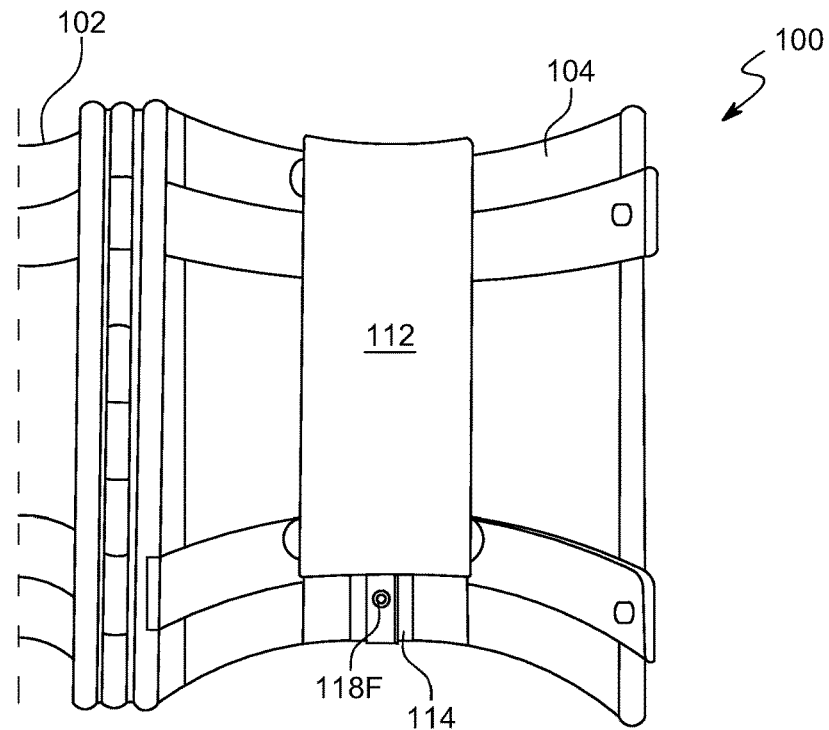
FIG. 9A shows an adjustable splint secured to a splint adjustment strip of a sleeve half, in accordance with one embodiment of the present invention.
Figure 9B:
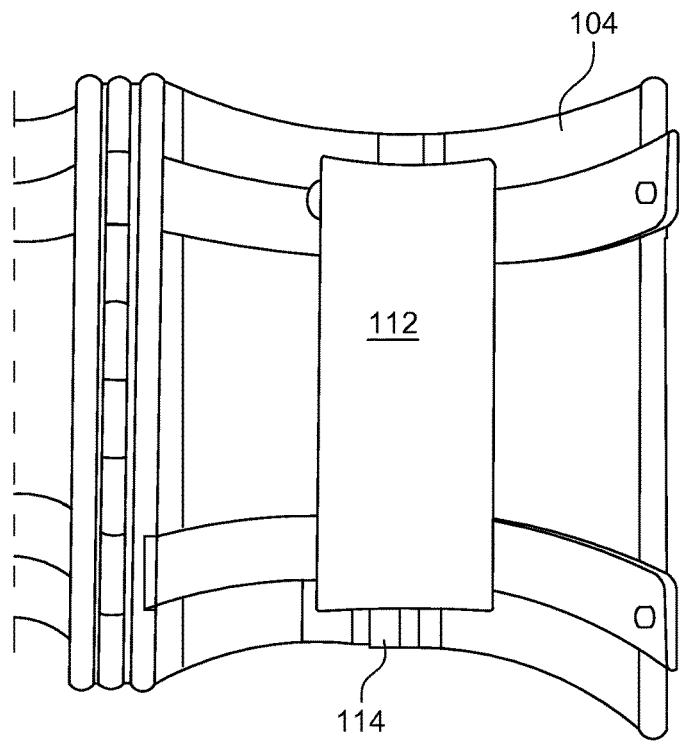
FIG. 9B shows the adjustable splint of FIG. 9A secured to the splint adjustment strip at a different location from that shown in FIG. 9A.

Referring to FIGS. 9A and 9B, in one embodiment, the position at which the splint 112 is mounted onto the sleeve may be adjusted between the upper and lower ends of the sleeve halves 102, 104. Referring to FIG. 9A, in one embodiment, the second adjustable splint 112 is snap-fit to the adjustment holes 118 provided along the length of the splint adjustment strip 114 so that the second adjustable splint is adjacent the upper end of the second sleeve half 104. Thus, in FIG. 9A, the second adjustable splint 112 is at an upper-most position relative to the splint adjustment strip 114. In FIG. 9B, the second adjustable splint 112 has been lowered one position along the length of the splint adjustment strip 114. As a result, the second adjustable splint 112 is closer to the lower end of the second sleeve half 104 in FIG. 9B than the position shown in FIG. 9A. Although the present invention is not limited by any particular theory of operation, it is believed that the ability to adjust the position of the splint 112 between the upper and lower ends of the second sleeve half 104 provides the ability to enhance comfort and efficacy when the splint is positioned over the outer surface of an animal's appendage. If medical personnel or an owner determines that the position of the splint 112 is causing discomfort, bruising, irritation, and/or an unsanitary condition, the position of the splint 112 may be adjusted to maximize safety, efficacy, and comfort.

Figure 10A:
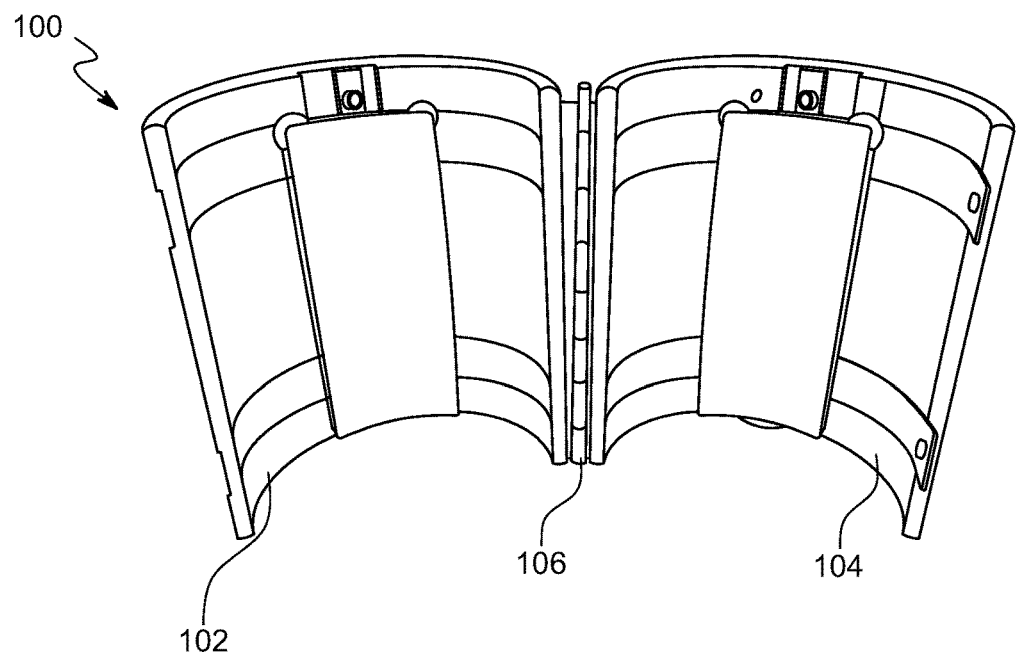
FIG. 10A shows the protective shield of FIG. 5 with the first and second adjustable splints secured to the respective first and second sleeve halves, in accordance with one embodiment of the present invention.
Figure 10B:
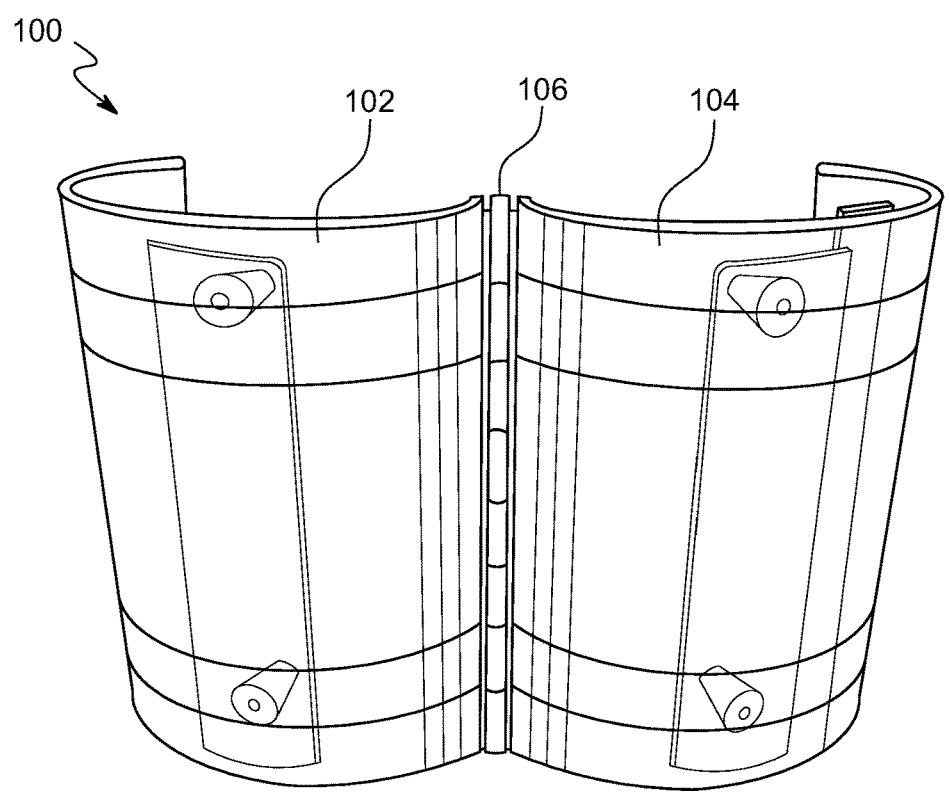
FIG. 10B shows a rear view of the protective shield shown in FIG. 10A.

Referring to FIGS. 10A and 10B, in one embodiment, the first and second sleeve halves 102, 104 are coupled together via the hinge 106 that enables the protective shield 100 to be moved between open and closed positions. In FIGS. 10A and 10B, the first and second sleeve halves 102, 104 are in the open configuration. FIG. 10B shows the outer surfaces of the respective first and second sleeve halves 102, 104, including the hinge 106 extending therebetween that enables the protective shield to more between open and closed configurations.

Figure 11:
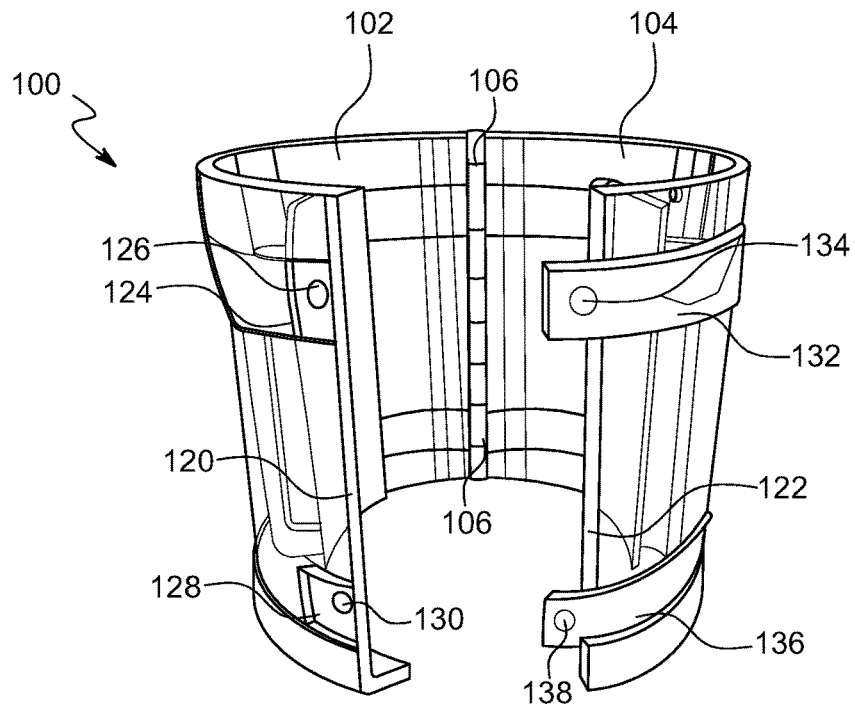
FIG. 11 shows the first and second sleeve halves of FIG. 5 partially closed towards one another.

Referring to FIG. 11, in one embodiment, the protective shield 100 may be moved into a closed configuration by pivoting the first and second sleeve halves 102, 104 about the hinge 106 for moving the opposing, free edges 120, 122 of the first and second sleeve halves 102, 104 toward one another. As shown in FIG. 11, the first securing band 132 of the second sleeve half 104 and the first recess 124 of the first sleeve half 102 are aligned with one another for mating when the protective shield 100 is in a closed configuration. Similarly, the second band 136 of the second sleeve half 104 is aligned with the second recess 128 of the first sleeve half 102 for mating together when the protective shield 100 is in a closed configuration.

The first and second projections 134, 138 at the free ends of the bands 132, 136 are adapted to be seated within the openings 126, 130 formed in the respective recesses 124, 128 for forming a snap-fit connection or lock therebetween.

Figure 12A:
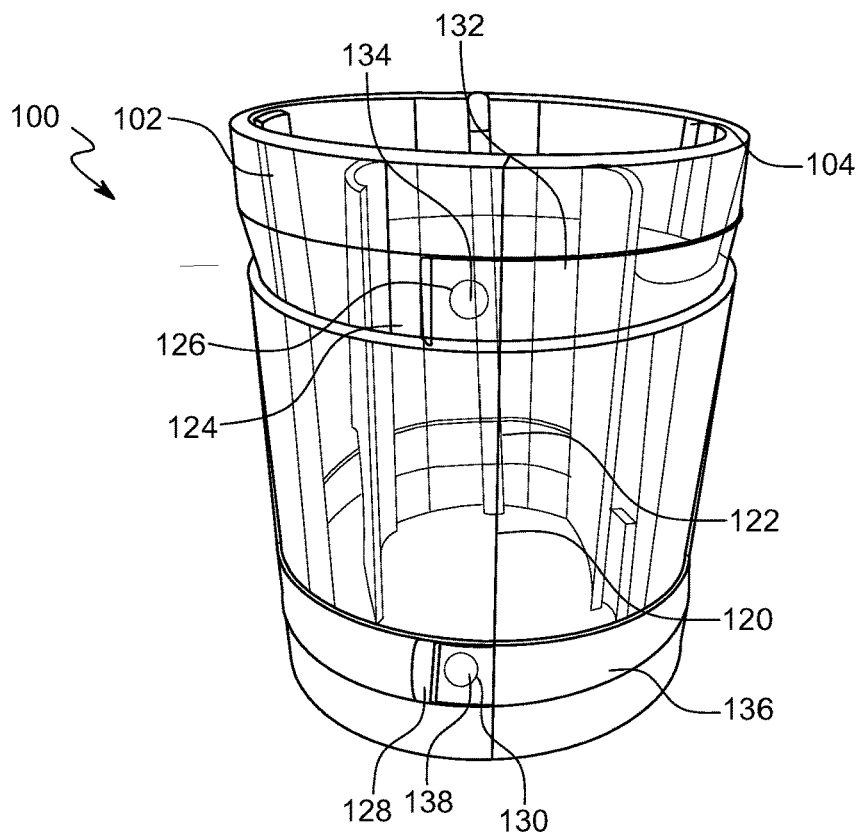
FIGS. 12A-12C show the protective shield after the first and second sleeve halves have been fully closed onto one another.
Figure 12B:
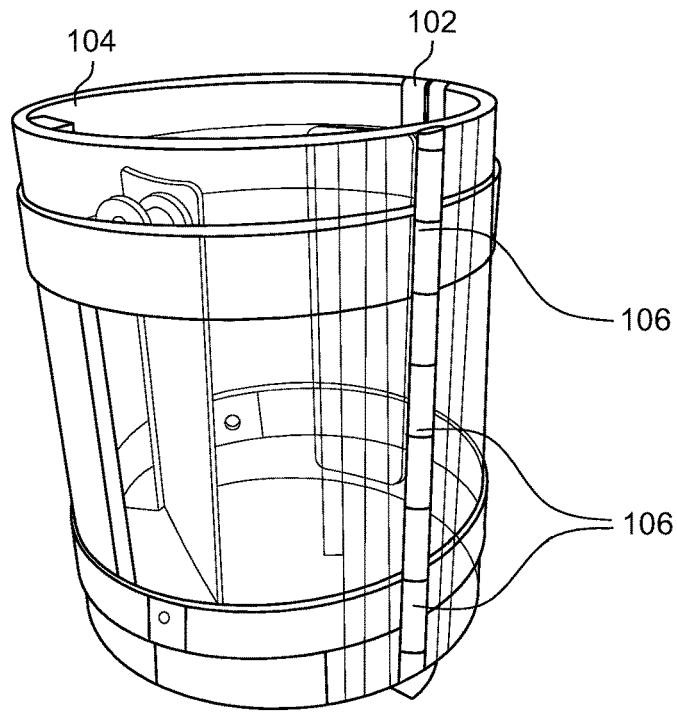

FIG. 12A shows the protective shield 100 in the closed configuration. The free edge 120 of the first sleeve half 102 is in contact with or abuts the free edge 122 of the second sleeve half 104. The free end of the first band 132 sits within the first recess 124 and the first projection 134 is inserted into the first opening 126 of the recess 124 for holding the protective shield 100 in the closed configuration. Similarly, the free end of the second band 136 is seated within the second recess 128 and the second projection 138 is inserted into the second opening 130 for holding the first and second sleeve halves 102, 104 in the closed configuration. In order to reopen the protective sleeve 100, the free ends of the first and second bands 132, 136 may be pried or pulled away from the respective recesses 124, 128 so that the first and second projections 134, 138 are retracted from the openings 126, 130. The hinge 106 enables the first and second sleeve halves 102, 104 to be swung or pivoted away from one another for returning the protective sleeve 100 to the open configuration shown in FIGS. 10A and 10B above. FIG. 12B shows the hinge 106 when the first and second sleeve halves 102, 104 are in a closed configuration. In one embodiment, the hinge 106 extends between the upper and lower ends of the respective first and second sleeve halves 102, 104.

Figure 12C:
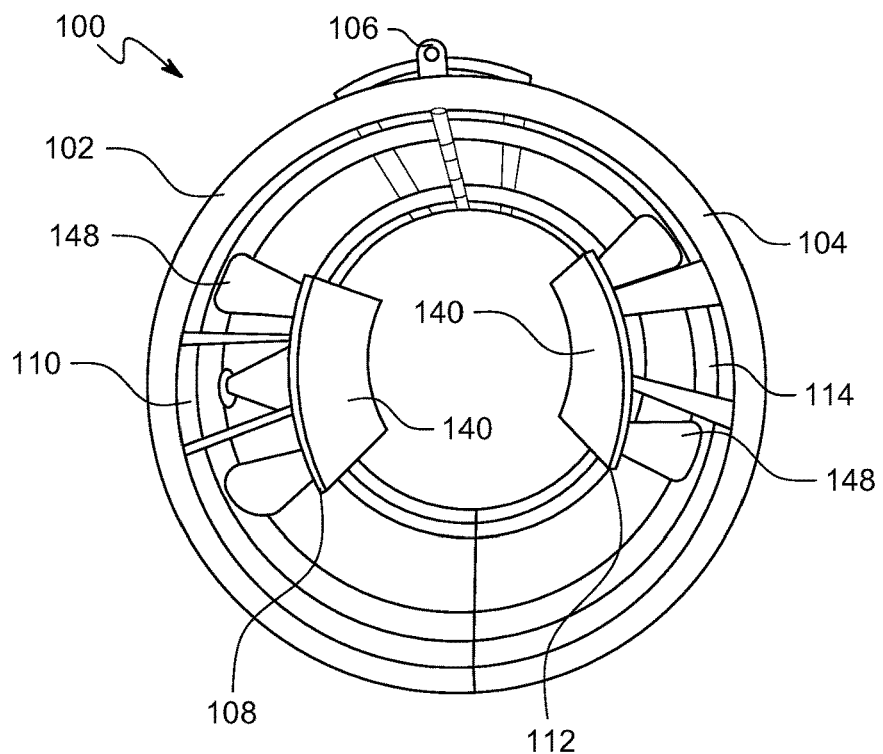

Referring to FIG. 12C, in one embodiment, the first adjustable splint 108 is secured to the inside of the first sleeve half 102. The support legs 148 have sloping bottom surfaces that generally conform to the interior curve surface of the first sleeve half 102. The top surface 140 of the first splint preferably defines a concave curved surface that extends along the length of the first adjustable splint 108. The second adjustable splint 112 is secured to the inner surface of the second sleeve half 104. In one embodiment, the top surface 140 of the second adjustable splint 112 opposes the top surface 140 of the first adjustable splint 108. In one embodiment, the top surface 140 of the second adjustable splint 112 has a concave curve surface that extends between the first and second ends of the second adjustable splint 112. As described above for the first adjustable splint 108, the second adjustable splint 112 has support legs 148 having lower extends defining sloping surfaces that generally conform to the shape of the inner surface of the second sleeve half 108 to provide stability for the second adjustable splint 112.

In one embodiment, the positions of the first and second adjustable splints 108, 112 may be adjusted between the respective upper and lower ends of the first and second sleeve halves 102, 104. The first sleeve half 102 preferably includes a first splint adjustment strip 110 that enables the position of the first adjustable splint 108 to be adjusted. The second splint adjustment strip 114 enables the position of the second adjustable splint 112 to be adjusted between the upper and lower ends of the second sleeve half 104. The positions of the first and second adjustable splints 108, 112 may be adjusted independently of one another so as to enhance the comfort, safety, and efficacy of the protective shield 100.

Figure 13:
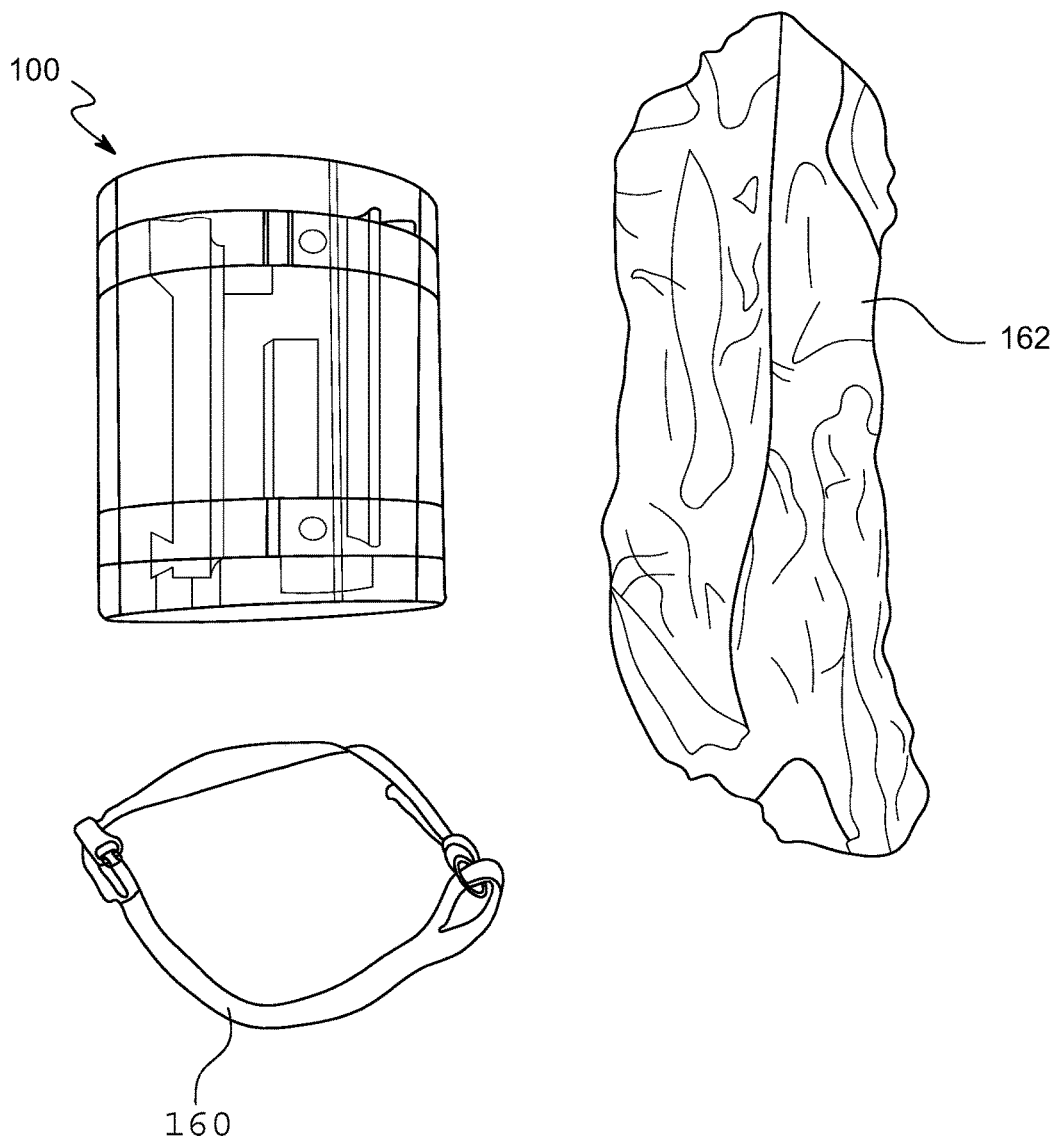
FIG. 13 shows a protective shield including an outer, adjustable strap that may be secured about the first and second sleeve halves and a water-proof cover that may be secured over the protective shield, in accordance with one embodiment of the present invention.

Referring to FIG. 13, in one embodiment, after the protective shield 100 has been positioned about the limb of an animal and closed, a flexible, adjustable strap 170 may be secured around the outer surface of the protective shield. In one embodiment, a waterproof cover or weather sleeve 162 may be secured about the closed protective shield 100. In one embodiment, the weather sleeve 162 preferably extends above and below the upper and lower ends of the closed protective shield 100. In one embodiment, the weather sleeve 162 may include strips having hook and loop fasteners for opening and closing the weather sleeve around the outer surface of the protective shield 100. Although the present invention is not limited by any particular theory of operation, it is believed that the utilization of a weather sleeve 162 about the outer surface of the protective shield 100 will enable an animal to utilize the protective shield in all types of weather including snow and rain.

Figure 14A:
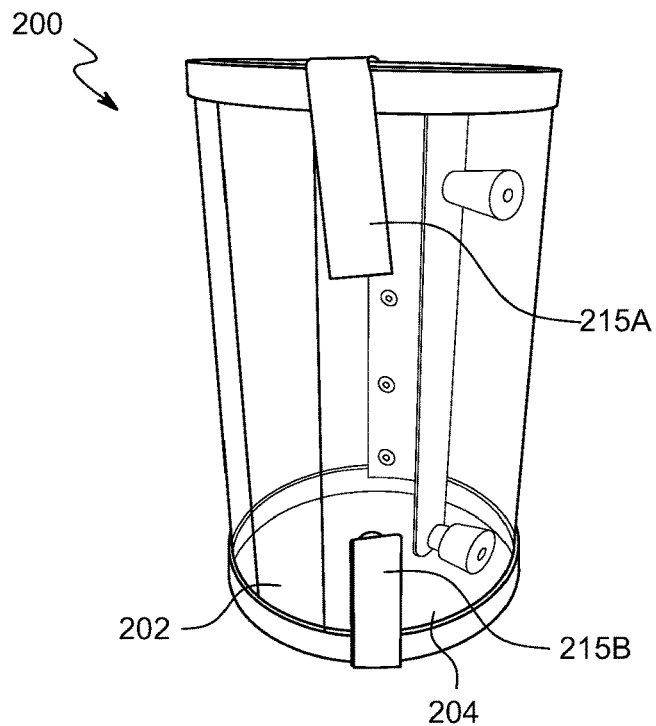
FIGS. 14A and 14B show a protective shield, in accordance with another embodiment of the invention.
Figure 14B:
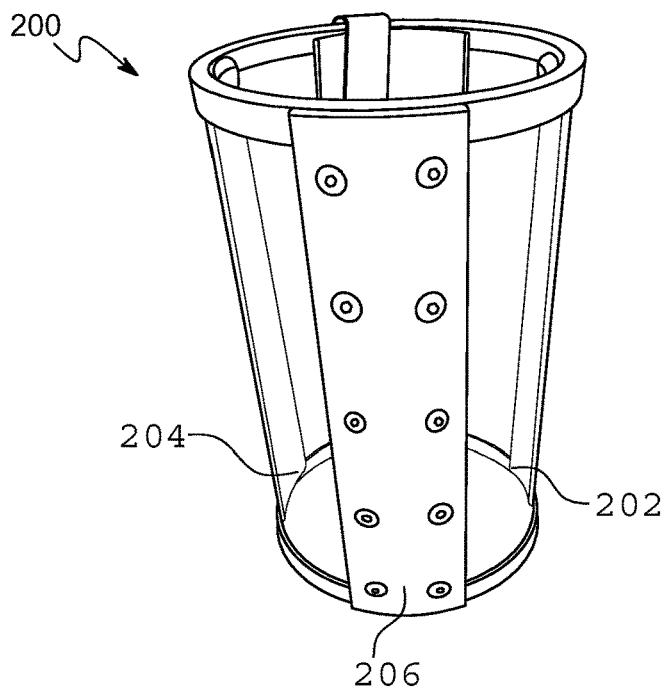

Referring to FIGS. 14A and 14B, in one embodiment, a protective shield 200 for the limb or appendage of an animal preferably includes a first sleeve half 202 and a second sleeve half 204 that may be moved between an open configuration and a closed configuration. The first and second sleeve halves 202, 204 are desirably connected together via a flexible hinge 206 that extends from the upper end to the lower end of the protective shield 200 for enabling the first and second sleeve halves 202, 204 to be open and closed relative to one another. In one embodiment, the protective shield 200 includes a pair of clips 215A, 215B that may be utilized for securing the first and second sleeve halves 202, 204 in the closed configuration. In one embodiment, a first clip 215A is desirably secured adjacent an upper end of the protective shield 200 and a second clip 215B is desirably secured adjacent a lower end of the protective shield 200.

Figure 15A:
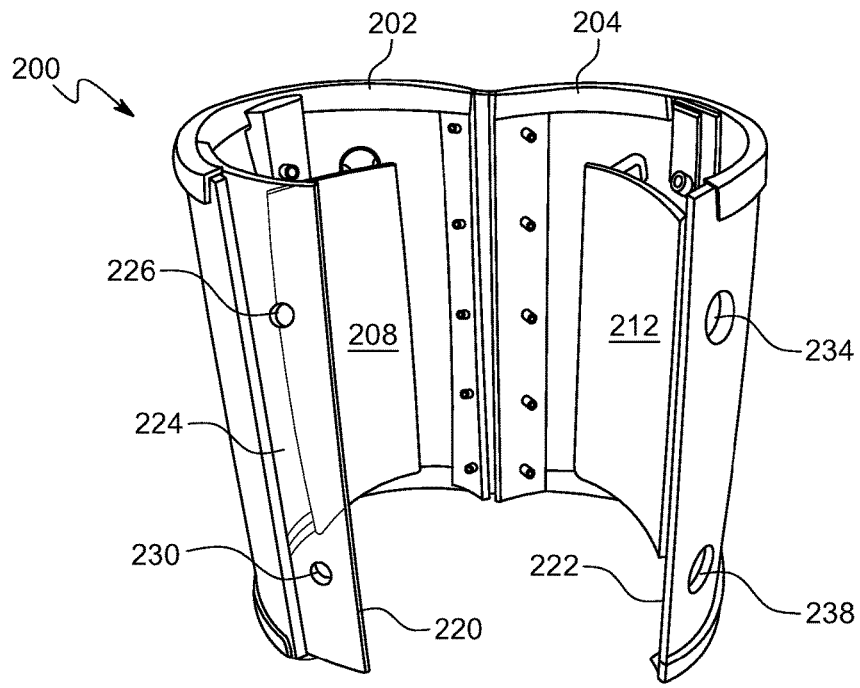
FIGS. 15A and 15B show the protective shield of FIGS. 14A-14B with the first and second sleeve halves in an open configuration.
Figure 15B:
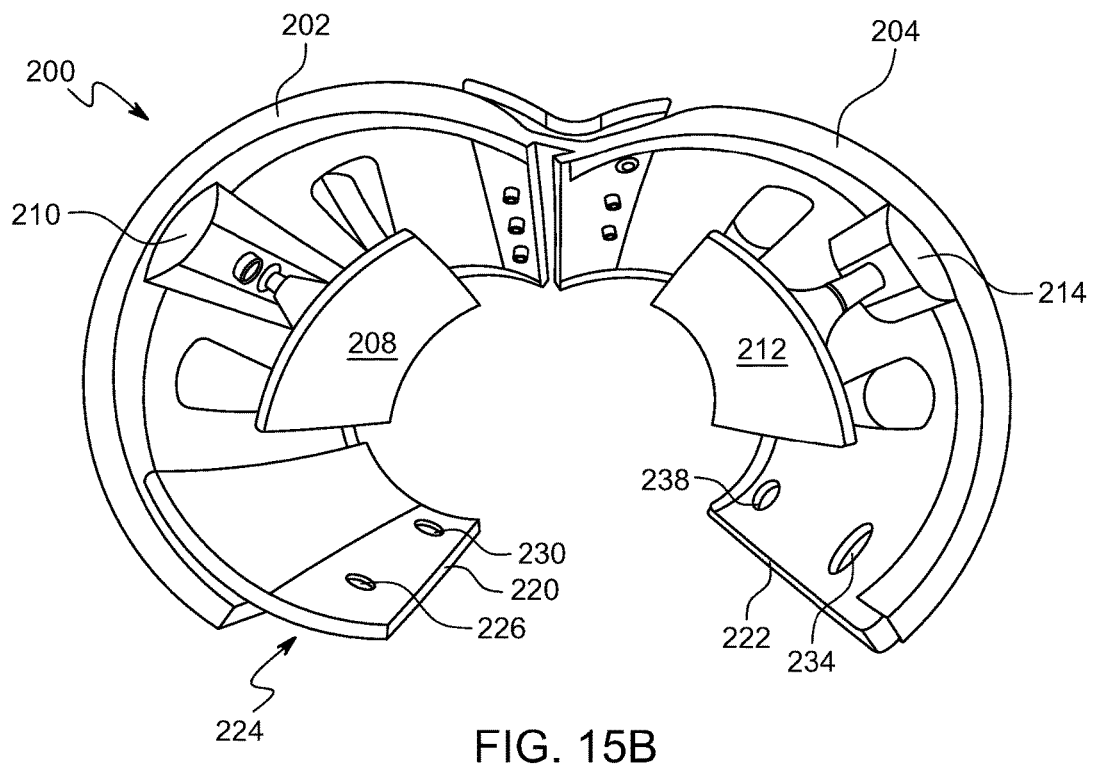

Referring to FIGS. 15A and 15B, in one embodiment, the first sleeve half 202 has a free edge 220 and the second sleeve half 204 has an opposing free edge 222. The first sleeve half 202 has a recessed area 224 including a first opening 226 and a second opening 230. The first and second openings 226, 230 are preferably vertically aligned with one another adjacent the free edge 220 of the first sleeve half 202.

In one embodiment, the second sleeve half 204 preferably includes a first supplemental opening 234 and a second supplemental opening 238 adjacent the free edge 222. In one embodiment, when the first and second sleeve halves 202, 204 are moved into a closed configuration, the free edge 222 of the second sleeve half 204 slides over the recess 222 of the first sleeve half 202 with the first opening 222 of the first sleeve half and the first supplemental opening 234 of the second sleeve half being aligned with one another, and the second opening 230 of the first sleeve half and the second supplemental opening 238 of the second sleeve half being aligned with one another. The above mentioned securing clips 215A, 215B (FIG. 14A) are desirably utilized for passing through the aligned openings 226, 234 and 230, 238 for holding the first and second sleeve halves 202, 204 in a closed configuration.

In one embodiment, the underside of the first adjustable splint 208 is secured to the first splint adjustment strip 210 of the first sleeve half 202 and the second adjustable splint 212 is secured to the second splint adjustment strip 214 of the second sleeve half 204. In one embodiment, the first and second adjustable splints 208, 212 are snap-fit to the openings extending along the lengths of the respective first and second splint adjustment strips 210, 214.

Figure 16A:
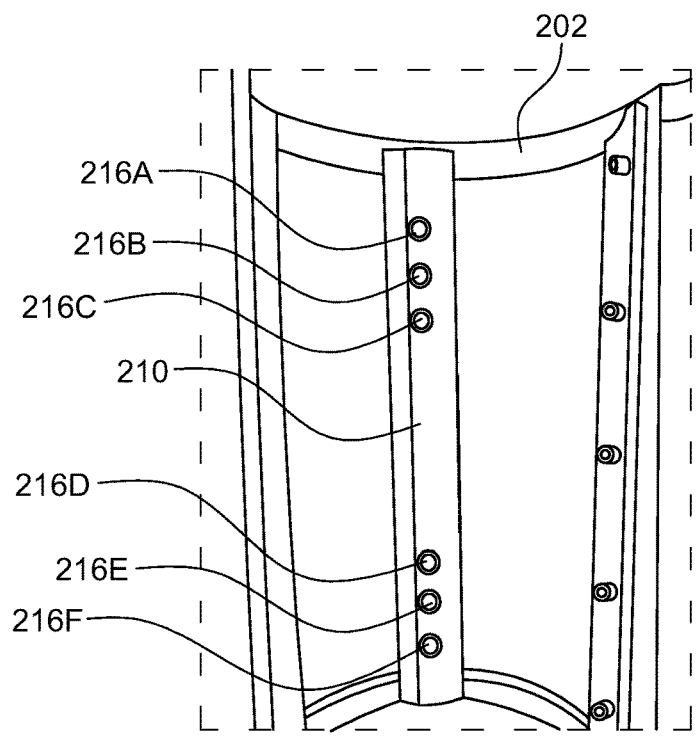
FIG. 16A shows a first sleeve half of the protective shield shown in FIG. 15A including a splint adjustment strip having a series of vertically aligned adjustment holes.
Figure 16B:
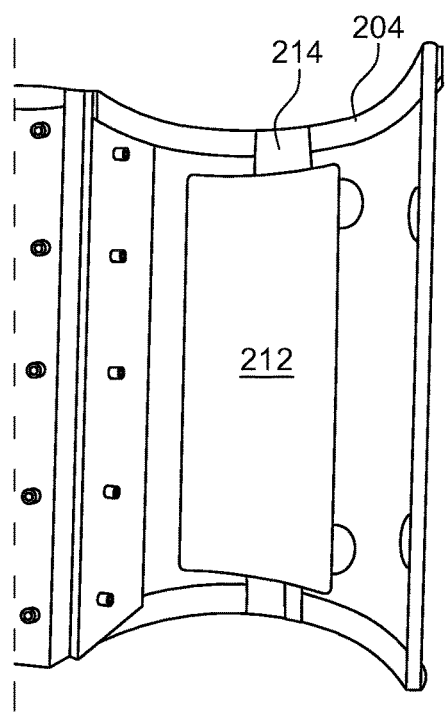
FIG. 16B shows an adjustable splint secured to the splint adjustment strip of FIG. 16A.

Referring to FIG. 16A, in one embodiment, the first sleeve half 202 includes the first splint adjustment strip 210 having a plurality of openings 216A-216F spaced from one another along the length of the first splint adjustment strip 210. The openings 216A-216F are preferably vertically aligned with one another along the length of the strip 210. In one embodiment, locking projections extending from the bottom surfaces of the adjustable splints are preferably inserted into the openings 216A-216D to form snap-fit connections between the adjustable splints and the splint adjustment strips. FIG. 16B shows the second adjustable splint 212 after it has formed a snap-fit connection with the second splint adjustment strip 214. The plurality of openings provided along the length of the second splint adjustment strip 214 allow the position of the adjustable splint 212 to be modified and/or adjusted between the upper and lower ends of the second sleeve half 204.

Figure 17:
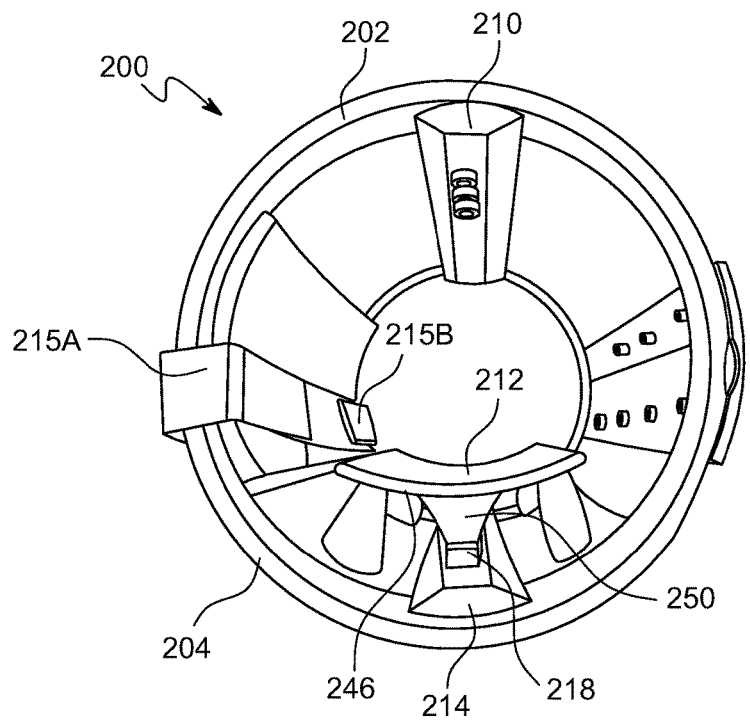
FIG. 17 shows a top view of the protective shield shown in FIGS. 14A and 14B with an adjustable splint secured to one of the splint adjustment strips.

FIG. 17 shows the protective shield 200 in a closed configuration with the opposing edges 220, 222 (FIG. 15B) of the first and second sleeve halves 202, 204 adjacent one another. The first and second clips 215A, 215B are secured over the aligned openings at the upper and lower ends of the respective first and second sleeve halves 202, 204. In FIG. 17, the second adjustable splint 212 is secured to the second splint adjustment strip 214. The projection 250 extending from the bottom surface 246 of the second adjustable splint 212 forms a snap-fit connection with an opening 218 provided along the length of the second strip 214. In FIG. 17, the first adjustable splint 208 (FIG. 15B) has been removed. In one embodiment, the protective shield 200 may be utilized with only one of the adjustable splints secured to the first and second sleeve halves 202, 204.

Figure 18:
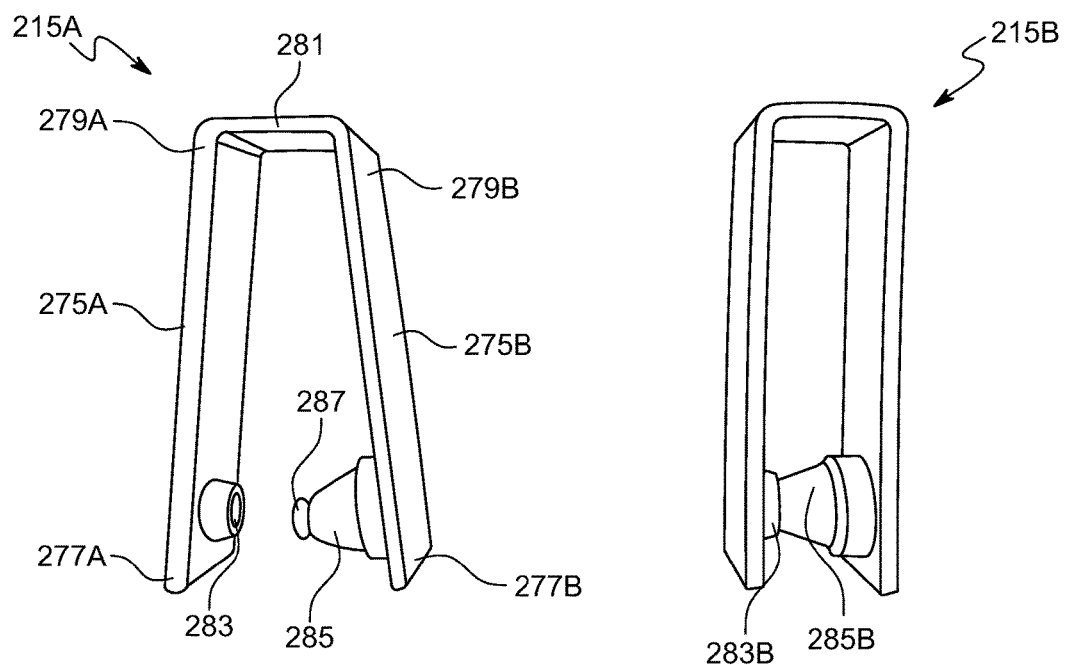
FIG. 18 shows snap clips utilized to secure the first and second sleeve halves of the protective shield of FIG. 14A together.

Referring to FIG. 18, in one embodiment, a protective shield is maintained in a closed configuration by a pair of locking clips 215A, 215B. In one embodiment, a first locking clip 215A preferably includes a first leg 275A having a first free end 277A and a second closed end 279A. The securing clip 215A includes a second leg 275B having a first free end 277B and a second closed end 279B. An interconnecting flange 281 interconnects the second closed ends 279A, 279B of the first and second legs 275A, 275B. The inner surface of the first leg 275A includes an opening 283 and the inner surface of the second leg 275B includes a projection 285 having a knob 287 that is adapted to be seated within the opening 283 to form a snap-fit connection between the projection 285 and the opening 283. In FIG. 18, the first locking clip 218A is an open configuration so that an upper edge of the protective shield may slide between the opposing inner surfaces of the first and second legs 275A, 275B. The opening 283 and the projection 285 are preferably aligned with openings formed in the first and second sleeve halves and the knob 287 is passed through the openings for securing the first and second sleeve halves in a closed configuration as describes herein. In FIG. 18, the second clip 215B is in a closed configuration with the knob of the projection 285B inserted into the opening 283B for forming a snap-fit connection therewith.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A protective shield having a tubular shape for protecting a wound on a limb of an animal, said protective shield comprising:
   a first sleeve half having a semi-cylindrical shape and a second sleeve half having a semi-cylindrical shape that are adapted to be joined together for forming a tubular shaped protective shield, wherein inner surfaces of said first and second sleeve halves define a central opening adapted to receive a limb of an animal;
   a first splint configured to be secured to said first sleeve half, said first splint having an arc-shaped body with a top surface having a concave shape that is adapted to contact the limb of said animal;
   a first splint attachment strip secured to the inner surface of said first sleeve half and extending between upper and lower ends of said first sleeve half, wherein said first splint attachment strip has a plurality of splint mounting positions provided thereon for securing said first splint to said first sleeve half at different locations between the upper and lower ends of said first sleeve half.

2. The protective shield as claimed in claim 1, wherein said plurality of splint mounting positions on said first splint attachment strip comprise a first mounting position for securing said first splint to said first sleeve half at a first location that is closer to the upper end of said first sleeve half, a second mounting position for securing said first splint to said first sleeve half at a second location that is equidistant from the upper and lower ends of said first sleeve half, and a third mounting position for securing said first splint to said first sleeve half at a third location that is closer to the lower end of said first sleeve half.

3. The protective shield as claimed in claim 2, wherein said first splint further comprises:
   a bottom surface that faces away from said top surface of said first splint, said bottom surface being spaced from and opposing the inner surface of said first sleeve half;
   first splint support legs projecting from said bottom surface of said first splint, said first splint support legs having lower ends that slope for conforming to the shape of the inner surface of said first sleeve half;
   first splint locking projections extending from said bottom surface of said first splint, wherein said first splint locking projections are configured for forming a snap-fit connection with said splint mounting positions provided on said first splint attachment strip.

4. The protective shield as claimed in claim 3, further comprising:
   a second splint configured to be secured to said second sleeve half for opposing said first splint, said second splint having an arc-shaped body with a top surface having a concave shape that is adapted to contact the limb of said animal;
   a second splint attachment strip secured to the inner surface of said second sleeve half and extending between upper and lower ends of said second sleeve half, wherein said second splint attachment strip has a plurality of splint mounting positions provided thereon for securing said second splint to said second sleeve half at different locations between the upper and lower ends of said second sleeve half.

5. The protective shield as claimed in claim 4, wherein said splint mounting positions on said second splint attachment strip comprise a first mounting position for securing said second splint to said second sleeve half at a first location that is closer to the upper end of said second sleeve half, a second mounting position for securing said second splint to said second sleeve half at a second location that is equidistant from the upper and lower ends of said second sleeve half, and a third mounting position for securing said second splint to said second sleeve half at a third location that is closer to the lower end of said second sleeve half.

6. The protective shield as claimed in claim 5, wherein said second splint further comprises:
   a bottom surface that faces away from said top surface of said second splint, said bottom surface being spaced from and opposing the inner surface of said second sleeve half;
   second splint support legs projecting from said bottom surface of said second splint, said second splint support legs having lower ends that slope for conforming to the shape of the inner surface of said second sleeve half;
   second splint locking projections extending from said bottom surface of said second splint, wherein said second splint locking projections are configured for forming a snap-fit connection with said splint mounting positions provided on said second splint attachment strip.

7. The protective shield as claimed in claim 1, further comprising a hinge connecting said first and second sleeve halves together for enabling said protective shield to move between open and closed positions.

8. The protective shield as claimed in claim 7, wherein said first and second sleeve halves have opposing free edges that are spaced from one another when said protective shield is in the open position and abut one another when said protective shield is in the closed position.

9. The protective shield as claimed in claim 8, further comprising:
   a first securing band provided on said second sleeve half, said first securing band having a free end that extends beyond the free edge of said second sleeve half;
   a first recess formed in an outer surface of said first sleeve half that extends to the free edge of said first sleeve half, wherein when said protective shield is in the closed position said free end of said first securing band is seated in said first recess formed in the outer surface of said first sleeve.

10. The protective shield as claimed in claim 9, further comprising:
    a first locking projection extending from said free end of said first securing band;
    a first locking hole formed in said first recess, wherein said first locking projection on said first securing band is inserted into said first locking hole formed in said first recess for holding said protective shield in the closed position.

11. The protective shield as claimed in claim 10, further comprising:
   a second securing band provided on said second sleeve half, said second securing band having a free end that extends beyond the free edge of said second sleeve half;
   a second recess formed in the outer surface of said first sleeve half that extends to the free edge of said first sleeve half, wherein when said protective shield is in the closed position said free end of said second securing band is seated in said second recess formed in the outer surface of said first sleeve.

12. The protective shield as claimed in claim 11, further comprising:
   a second locking projection extending from said free end of said second securing band;
   a second locking hole formed in said second recess, wherein said second locking projection on said second securing band is inserted into said second locking hole formed in said second recess for holding said protective shield in the closed position.

13. The protective shield as claimed in claim 1, wherein said protective shield is transparent and made of polymer materials.

14. The protective shield as claimed in claim 1, further comprising a pad secured over said top surface of said first splint.

15. The protective shield as claimed in claim 14, wherein said pad is selected from the group consisting of gauze, cushioning, surgical mesh, and sanitary dressings.

16. A protective shield having a tubular shape for protecting a wound on a limb of an animal, said protective shield comprising:
   a first sleeve half having a semi-cylindrical shape and a second sleeve half having a semi-cylindrical shape;
   a hinge connecting said first and second sleeve halves together for enabling said protective shield to move between open and closed positions, wherein inner surfaces of said first and second sleeve halves define a central opening adapted to receive a limb of an animal;
   a first splint overlying the inner surface of said first sleeve half, said first splint having an arc-shaped body with a top surface having a concave shape that is configured to contact the limb of said animal;
   a first splint attachment strip secured to the inner surface of said first sleeve half and extending between upper and lower ends of said first sleeve half, wherein said first splint attachment strip has a plurality of splint mounting positions provided thereon for securing said first splint to said first sleeve half at different locations between the upper and lower ends of said first sleeve half;
   a second splint overlying the inner surface of said second sleeve half, said second splint having an arc-shaped body with a top surface having a concave shape that is configured to contact the limb of said animal;
   a second splint attachment strip secured to the inner surface of said second sleeve half and extending between upper and lower ends of said second sleeve half, wherein said second splint attachment strip has a plurality of splint mounting positions provided thereon for securing said second splint to said second sleeve half at different locations between the upper and lower ends of said second sleeve half.

17. The protective shield as claimed in claim 16, further comprising:
   said splint mounting positions on said first splint attachment strip comprising a first mounting position for securing said first splint to said first sleeve half at a first location that is closer to the upper end of said first sleeve half, a second mounting position for securing said first splint to said first sleeve half at a second location that is equidistant from the upper and lower ends of said first sleeve half, and a third mounting position for securing said first splint to said first sleeve half at a third location that is closer to the lower end of said first sleeve half; and
   said splint mounting positions on said second splint attachment strip comprising a first set of mounting holes for securing said second splint to said second sleeve half at a first location that is closer to the upper end of said second sleeve half, a second set of mounting holes for securing said second splint to said second sleeve half at a second location that is equidistant from the upper and lower ends of said second sleeve half, and a third set of mounting holes for securing said second splint to said second sleeve half at a third location that is closer to the lower end of said second sleeve half.

18. The protective shield as claimed in claim 17,
   said first splint further comprising a bottom surface that faces away from said top surface of said first splint, said bottom surface being spaced from and opposing the inner surface of said first sleeve half, first splint support legs projecting from said bottom surface of said first splint, said first splint support legs having lower ends that slope for conforming to the shape of the inner surface of said first sleeve half, and first splint locking projections extending from said bottom surface of said first splint, wherein said first splint locking projections are configured for forming a snap-fit connection with said splint mounting positions on said first splint attachment strip;
   said second splint further comprising a bottom surface that faces away from said top surface of said second splint, said bottom surface being spaced from and opposing the inner surface of said second sleeve half, second splint support legs projecting from said bottom surface of said second splint, said second splint support legs having lower ends that slope for conforming to the shape of the inner surface of said second sleeve half, and second splint locking projections extending from said bottom surface of said second splint, wherein said second splint locking projections are configured for forming a snap-fit connection with said mounting positions on said second splint attachment strip.

19. The protective shield as claimed in claim 18, further comprising:
   said first and second sleeve halves having opposing free edges that are spaced from one another when said protective shield is in the open position and abut one another when said protective shield is in the closed position;
   a first securing band provided on said second sleeve half adjacent the upper end of said second sleeve half, said first securing band having a free end that extends beyond the free edge of said second sleeve half;
   a first recess formed in an outer surface of said first sleeve half that extends to the free edge of said first sleeve half, wherein when said protective shield is in the closed position said free end of said first securing band is seated in said first recess formed in the outer surface of said first sleeve;

a second securing band provided on said second sleeve half adjacent the lower end of said second sleeve half, said second securing band having a free end that extends beyond the free edge of said second sleeve half;

a second recess formed in the outer surface of said first sleeve half that extends to the free edge of said first sleeve half, wherein when said protective shield is in the closed position said free end of said second securing band is seated in said second recess formed in the outer surface of said first sleeve.

20. The protective shield as claimed in claim 16, further comprising pads secured over said top surfaces of said first and second splints, wherein said pads are selected from the group consisting of gauze, cushioning, surgical mesh, and sanitary dressings.

\* \* \* \* \*